(12) United States Patent
Rogers et al.

(10) Patent No.: US 8,832,894 B2
(45) Date of Patent: Sep. 16, 2014

(54) CLEANING DEVICE FOR MALE END OF INTRAVENEOUS SET

(75) Inventors: Bobby E. Rogers, San Diego, CA (US); Paul DiPerna, San Diego, CA (US); Gino Kang, Ir, CA (US); Christine Arme, Carlsbad, CA (US)

(73) Assignee: Ivera Medical Corporation, San Diego, CA (US)

( * ) Notice: Subject to any disclaimer, the term of this patent is extended or adjusted under 35 U.S.C. 154(b) by 0 days.

(21) Appl. No.: 13/553,627

(22) Filed: Jul. 19, 2012

(65) Prior Publication Data

US 2013/0019421 A1 Jan. 24, 2013

Related U.S. Application Data

(60) Provisional application No. 61/509,460, filed on Jul. 19, 2011.

(51) Int. Cl.
*A61M 5/315* (2006.01)

(52) U.S. Cl.
USPC .................. 15/104.03; 15/104.05; 15/104.93; 604/187

(58) Field of Classification Search
CPC ................................ A61M 5/315; A61M 5/32
USPC ............... 15/104.03, 104.05, 104.93, 104.94, 15/210.1; 604/199, 111; 134/84, 92, 136, 134/141, 201
See application file for complete search history.

(56) References Cited

U.S. PATENT DOCUMENTS

| | | |
|---|---|---|
| 1,744,026 A | 1/1930 | Baltzley |
| 1,841,597 A | 1/1932 | Hammer et al. |
| 1,937,492 A | 11/1933 | Merolle |
| 2,341,285 A | 2/1944 | Petrullo |
| 2,731,963 A | 1/1956 | Blank |
| 2,740,480 A * | 4/1956 | Cox .............................. 166/170 |

(Continued)

FOREIGN PATENT DOCUMENTS

| | | |
|---|---|---|
| DE | 2164821 A1 | 8/1972 |
| EP | 0462355 A1 | 12/1991 |

(Continued)

OTHER PUBLICATIONS

U.S. Appl. No. 60/815,806, Jun. 22, 2006, Anderson et al.

(Continued)

*Primary Examiner* — Monica Carter
*Assistant Examiner* — Michael Jennings
(74) *Attorney, Agent, or Firm* — Mintz Levin Cohn Ferris Glovsky and Popeo, P.C.

(57) ABSTRACT

A cleaning device includes a cap having an opening and that defines an inner cavity, and a channel that extends from a bottom of the inner cavity to a bottom of the cap. A plunger includes a domed top surface, a shoulder, and a rod member. The plunger moves toward the bottom of the cap as the domed top surface is contacted by a male protrusion of a male medical implement, to push the rod member and piercing end further into the channel. The crush ribs contact an inner surface of the channel to inhibit reverse movement of the plunger. A cleaning material contains a cleaning agent and is positioned around the rod member and compressed between the bottom of the inner cavity and the shoulder of the plunger to release the cleaning agent around the shoulder to contact the male protrusion.

4 Claims, 5 Drawing Sheets

(56) References Cited

U.S. PATENT DOCUMENTS

| | | | |
|---|---|---|---|
| 2,993,612 A | 7/1961 | Trautvetter | |
| 3,120,879 A | 2/1964 | Warner | |
| 3,362,587 A | 1/1968 | Postel et al. | |
| 3,391,847 A | 7/1968 | Christine et al. | |
| 3,405,831 A | 10/1968 | Hudson et al. | |
| 3,431,548 A | 3/1969 | Busier et al. | |
| 3,435,978 A | 4/1969 | Wittwer | |
| 3,443,686 A | 5/1969 | Raymond et al. | |
| 3,651,972 A | 3/1972 | Itoh | |
| 3,771,685 A | 11/1973 | Micallef | |
| 3,818,627 A | 6/1974 | Lebensfeld | |
| 3,979,001 A | 9/1976 | Bogert | |
| 3,987,921 A | 10/1976 | Aichinger | |
| 4,089,463 A | 5/1978 | Babiol | |
| 4,169,751 A | 10/1979 | Yen | |
| 4,257,526 A | 3/1981 | Weits et al. | |
| 4,280,632 A | 7/1981 | Yuhara | |
| 4,289,248 A | 9/1981 | Lynn | |
| 4,340,148 A | 7/1982 | Beckham | |
| 4,401,227 A | 8/1983 | Pehr | |
| 4,440,207 A | 4/1984 | Genatempo et al. | |
| 4,461,394 A | 7/1984 | Sendel et al. | |
| 4,564,116 A | 1/1986 | Prohaska | |
| 4,572,373 A | 2/1986 | Johansson | |
| 4,597,758 A | 7/1986 | Aalto et al. | |
| 4,671,306 A | 6/1987 | Spector | |
| 4,674,643 A | 6/1987 | Wilde et al. | |
| 4,712,705 A | 12/1987 | Fuehrer | |
| 4,752,983 A | 6/1988 | Grieshaber | |
| 4,778,447 A | 10/1988 | Velde et al. | |
| 4,798,303 A | 1/1989 | Arnold | |
| 4,991,629 A | 2/1991 | Ernesto et al. | |
| 5,078,693 A | 1/1992 | Shine | |
| 5,143,104 A | 9/1992 | Iba et al. | |
| 5,169,033 A | 12/1992 | Shay | |
| 5,184,742 A | 2/1993 | DeCaprio et al. | |
| 5,242,425 A | 9/1993 | White et al. | |
| 5,263,606 A | 11/1993 | Dutt et al. | |
| 5,292,020 A | 3/1994 | Narin | |
| 5,385,372 A | 1/1995 | Utterberg | |
| 5,385,378 A | 1/1995 | Hakamada et al. | |
| 5,398,837 A | 3/1995 | Degrassi | |
| 5,445,270 A | 8/1995 | Dratz | |
| 5,554,135 A | 9/1996 | Menyhay | |
| 5,702,017 A | 12/1997 | Goncalves | |
| 5,743,884 A | 4/1998 | Hasson et al. | |
| 5,792,120 A | 8/1998 | Menyhay | |
| 5,951,519 A | 9/1999 | Utterberg | |
| 5,954,957 A | 9/1999 | Chin-Loy et al. | |
| 6,004,299 A * | 12/1999 | Arai et al. | 604/218 |
| 6,045,539 A | 4/2000 | Menyhay | |
| 6,102,223 A | 8/2000 | Montgomery | |
| 6,116,468 A | 9/2000 | Nilson | |
| 6,227,391 B1 | 5/2001 | King | |
| 6,250,315 B1 | 6/2001 | Ernster | |
| 6,364,862 B1 | 4/2002 | Bonilla | |
| 6,523,686 B1 | 2/2003 | Bae | |
| 6,527,751 B2 * | 3/2003 | Fischer et al. | 604/218 |
| 6,622,882 B2 | 9/2003 | Smith | |
| 6,913,157 B2 | 7/2005 | Oh | |
| 7,188,623 B2 | 3/2007 | Anderson et al. | |
| 7,282,186 B2 | 10/2007 | Lake, Jr. et al. | |
| 7,329,235 B2 * | 2/2008 | Bertron et al. | 604/88 |
| 7,427,275 B2 * | 9/2008 | DeRuntz et al. | 604/207 |
| 7,500,964 B2 * | 3/2009 | Shaw et al. | 604/197 |
| 7,682,561 B2 | 3/2010 | Davis et al. | |
| 7,704,002 B2 | 4/2010 | Fisher et al. | |
| 7,780,794 B2 | 8/2010 | Rogers et al. | |
| 7,857,793 B2 | 12/2010 | Raulerson et al. | |
| 7,922,701 B2 | 4/2011 | Buchman | |
| 7,931,618 B2 * | 4/2011 | Wyrick | 604/117 |
| 7,931,877 B2 | 4/2011 | Steffens et al. | |
| 7,967,779 B2 * | 6/2011 | Bertron et al. | 604/89 |
| 7,985,302 B2 | 7/2011 | Rogers et al. | |
| 7,988,676 B1 * | 8/2011 | Gray | 604/199 |
| 8,061,544 B2 | 11/2011 | Frishman | |
| 8,105,293 B2 * | 1/2012 | Pickhard | 604/199 |
| 8,162,899 B2 | 4/2012 | Tennican | |
| 8,167,847 B2 | 5/2012 | Anderson et al. | |
| 8,172,813 B2 * | 5/2012 | Janish | 604/228 |
| 8,177,768 B2 | 5/2012 | Leinsing | |
| 8,197,749 B2 | 6/2012 | Howlett et al. | |
| 8,206,514 B2 | 6/2012 | Rogers et al. | |
| 8,231,587 B2 | 7/2012 | Solomon et al. | |
| 8,277,422 B2 * | 10/2012 | Oliver et al. | 604/218 |
| 8,287,491 B2 * | 10/2012 | Burns et al. | 604/110 |
| 8,296,893 B2 * | 10/2012 | Vinci et al. | 15/104.05 |
| 8,303,548 B2 * | 11/2012 | Ito et al. | 604/218 |
| 8,641,681 B2 | 2/2014 | Solomon et al. | |
| 8,647,326 B2 | 2/2014 | Solomon et al. | |
| 2002/0133124 A1 | 9/2002 | Leinsing et al. | |
| 2004/0024357 A1 * | 2/2004 | Pelkey et al. | 604/110 |
| 2004/0030321 A1 | 2/2004 | Fangrow | |
| 2004/0039341 A1 * | 2/2004 | Ranalletta | 604/199 |
| 2004/0195136 A1 | 10/2004 | Young et al. | |
| 2004/0258560 A1 | 12/2004 | Lake, Jr. et al. | |
| 2005/0147524 A1 | 7/2005 | Bousquet | |
| 2005/0147525 A1 | 7/2005 | Bousquet | |
| 2005/0214185 A1 | 9/2005 | Castaneda | |
| 2006/0030827 A1 | 2/2006 | Raulerson et al. | |
| 2006/0048313 A1 | 3/2006 | Yamaki | |
| 2007/0112333 A1 | 5/2007 | Hoang et al. | |
| 2008/0019889 A1 | 1/2008 | Rogers et al. | |
| 2008/0086091 A1 | 4/2008 | Anderson et al. | |
| 2008/0132880 A1 | 6/2008 | Buchman | |
| 2008/0177250 A1 | 7/2008 | Howlett et al. | |
| 2009/0028750 A1 | 1/2009 | Ryan | |
| 2009/0099529 A1 | 4/2009 | Anderson et al. | |
| 2009/0137969 A1 | 5/2009 | Colantonio et al. | |
| 2009/0205151 A1 | 8/2009 | Fisher et al. | |
| 2010/0000040 A1 | 1/2010 | Shaw et al. | |
| 2010/0047123 A1 | 2/2010 | Solomon et al. | |
| 2010/0050351 A1 | 3/2010 | Colantonio et al. | |
| 2010/0172794 A1 | 7/2010 | Ferlic et al. | |
| 2010/0174162 A1 * | 7/2010 | Gough et al. | 600/341 |
| 2010/0199448 A1 * | 8/2010 | Vazales et al. | 15/104.05 |
| 2010/0312197 A1 * | 12/2010 | Sano et al. | 604/220 |
| 2010/0313366 A1 | 12/2010 | Rogers et al. | |
| 2011/0213341 A1 | 9/2011 | Solomon et al. | |
| 2011/0265825 A1 | 11/2011 | Rogers et al. | |
| 2011/0277788 A1 | 11/2011 | Rogers et al. | |
| 2013/0019421 A1 | 1/2013 | Rogers et al. | |

FOREIGN PATENT DOCUMENTS

| | | |
|---|---|---|
| EP | 1061000 A2 | 12/2000 |
| EP | 1977714 A1 | 10/2008 |
| EP | 2135626 A1 | 12/2009 |
| JP | 07-047137 A | 2/1995 |
| JP | 07-043674 U | 9/1995 |
| JP | 09-206370 A | 8/1997 |
| JP | 2001-527441 A | 12/2001 |
| JP | 2002-291906 A | 10/2002 |
| JP | 4234777 B1 | 3/2009 |
| WO | WO-98/48872 A1 | 11/1998 |
| WO | WO-00/24442 A1 | 5/2000 |
| WO | WO-2007/103998 A2 | 9/2007 |
| WO | WO-2007/137056 A2 | 11/2007 |
| WO | WO-2009136957 A1 | 11/2009 |
| WO | WO-2011056221 A1 | 5/2011 |
| WO | WO-2011120017 A1 | 9/2011 |

OTHER PUBLICATIONS

U.S. Appl. No. 60/832,437, Jul. 21, 2006, Rogers.

Byington "Spontaneously Generating Life in Your Classroom? Pasteur, Spallanzani & Science Process," The American Biology Teacher, vol. 63, No. 5 (May 2001), published by University of California Press on behalf of National Association of Biology Teachers.

European Patent Office, Supplementary Partial European Search Report and Opinion for EP Application No. 07 75 8117 date of completion of the search Nov. 22, 2012, 6 pgs.

(56) References Cited

OTHER PUBLICATIONS

International Search Report and Written Opinion dated Jul. 22, 2009, PCT/US2008/053744.
International Standard ISO 594-2. "Conical Fitting with 6% (Luer) Taper for Syringes, Needles and Certain Other Medical Equipment—Part 2: Lock Fittings". Reference No. *ISO 594-2:1998(E). Second edition.* (Sep. 1, 1998)1:11.
Japanese Patent Office, Japanese Notice of Reasons for Rejection for Japanese Patent Application No. 2008-558527 dated Apr. 12, 2012.
Japanese Patent Office, Japanese Notice of Reasons for Rejection for Japanese Patent Application No. 2008-558527 dated Apr. 2, 2013.
Material Properties of Polyamide (Nylon), www.madeitfrom.com, pp. 1-2. Retrieved Sep. 23, 2012.
Material Properties of Polycarbonate, www.madeitfrom.com, pp. 1-3. Retrieved Sep. 23, 2012.
Material Properties of Polypropylene, www.madeitfrom.com, pp. 1-2. Retrieved Sep. 23, 2012.
Menyhay et al. "Disinfection of Needleless Catheter Connectors and Access Ports with Alcohol May Not Prevent Microbial Entry: The Promise of a Novel Antiseptic-Barrier Cap". *The University of Chicago Press on behalf of the Society for Healthcare Epidemiology of America. Infect Control Hosp Epidemiol* vol. 27(2006):23-27.
Menyhay Healthcare Systems LLC available at http://www.menyhaymedical.comimenyhay.html (retrieved Nov. 8, 2013).
PCT Search Report and Written Opinion dated Oct. 16, 2013 for PCT application No. PCT/US2013/044167.
The International Bureau of WIPO, PCT International Preliminary Report on Patentability and Written Opinion of the International Searching Authorityfor International Application No. PCT/US2007/063534 dated Nov. 21, 2007.
Value Plastics Inc, Luer Connectors, http://www.valueplasctics.com/search/search.aspx, pp. 1-2. Retrieved Sep. 23, 2012.
International Search Report and Written Opinion dated Nov. 9, 2012, PCT/US2012/025517.
European Patent Office, European Search Report and Opinion for EP Application No. EP 10 78 3956, date of completion of the search Mar. 12, 2014, 7 pgs.

* cited by examiner

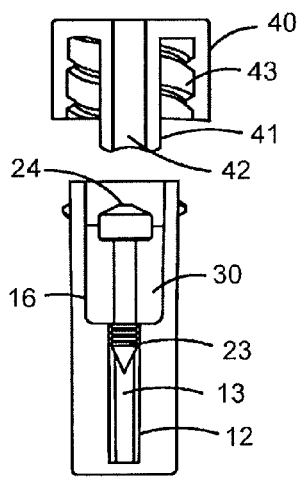 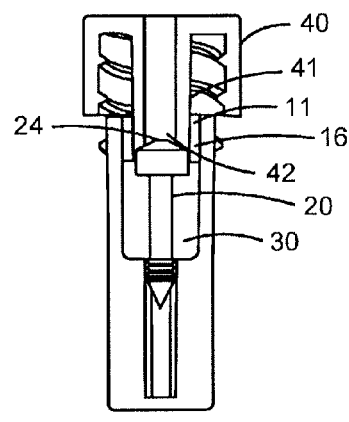 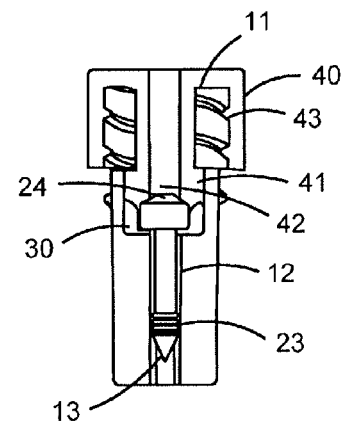
FIG. 5  FIG. 6  FIG. 7
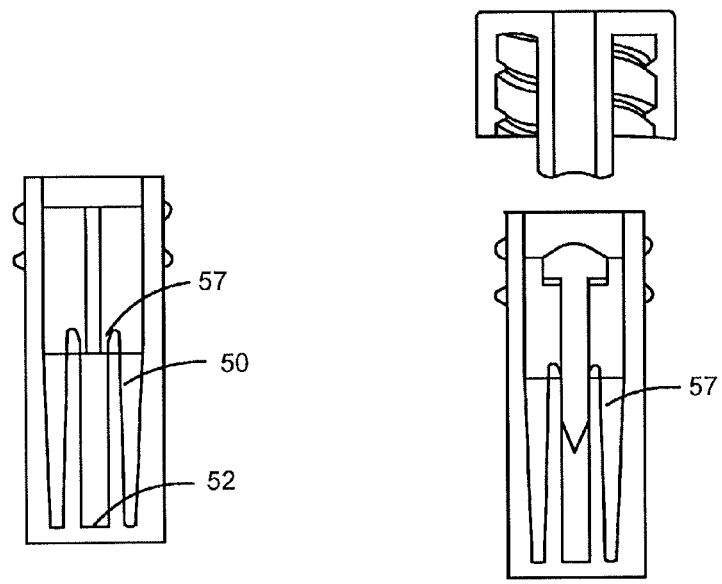
FIG. 8  FIG. 9

CLEANING DEVICE FOR MALE END OF INTRAVENEOUS SET

BACKGROUND

One conventional solution for protection of a male end of an intravenous (IV) device that is known as a "dual cap". This device has a cap used to disinfect luer access valves and has a second cap used to cap the male distal end of an IV. However, there is no one-to-one ratio of these two caps for a single access line female-to-male luer interface. Thus, many caps of this set of two caps will be wasted. Further, there is the issue of throwing away unused caps and their associated costs and inconvenience. Also, this system has too many parts, also adding to cost to manufacture.

SUMMARY

This document describes a cleaning device implemented as disinfecting caps. While some caps are designed for attachment to luer activated needle free valves to disinfect and protect them from contamination, the present disclosure describes a cap for BR attachment to the distal tip of an IV set. This distal tip is an open tab and is normally configured as a male luer lock or male luer slip. The cleaning device of the present application will attach to the male distal end of the IV set to disinfect and protect that tip from contamination. Outside of dimensional differences, several key features of the cleaning device include: Threads are located on an outside surface of the cap rather than inside as with other caps; and a friction based plunger internal to the cap is configured to act as a seal to prevent the chemical disinfecting agent from entering into the male distal end of the set. This plunger may or may not be a true seal, but should inhibit entrance of the chemical agent into the line.

Disinfection device for the distal tip of an IV set, in particular the male distal tip of the IV set, is preferably a single use disposable product with a removable foil-sealable opening, either individually sealed or sealed to a strip or plane of seal material. This device includes an IPA soaked sponge inside, and is made of materials compatible with IPA. The threading preferably meets the ISO standard(s) and allows the device to lock onto the distal male luer. In some implementations, the device is green in color. When attached to the distal end of an IV set, the IPA does not enter the fluid line, and can include an internal pin to seal the orifice. Further, the IV set's distal end and sidewalls of the male luer nozzle is be bathed in IPA when the cap is applied onto the luer.

In one aspect, a cleaning device for a male medical implement having a male protrusion, the cleaning device includes a cap that defines an inner cavity having a top and a bottom, the top of the inner cavity defining an opening. The cap further defines a channel that extends from the bottom of the inner cavity to a bottom of the cap, the channel having a diameter that is smaller than a diameter of the inner cavity. The cleaning device further includes a plunger in the inner cavity. The plunger includes a domed top surface, a shoulder below the domed top surface, and a rod member extending below the shoulder to a piercing end. The rod member further includes a number of crush ribs extending laterally from the rod member, the piercing end of the plunger extending into the channel such that the domed top surface and shoulder are positioned proximate the opening in an initial position. The plunger is configured to move toward the bottom of the cap as the domed top surface is contacted by the male protrusion of the male medical implement, to push the rod member and piercing end further into the channel, and such that the crush ribs contact an inner surface of the channel to inhibit reverse movement of the plunger. The cleaning device further includes a cleaning material around the rod member between the shoulder and the crush ribs, the cleaning material at least partially containing a cleaning agent. The cleaning material is compressed between the bottom of the inner cavity and the shoulder of the plunger to release the cleaning agent around the shoulder to contact the male protrusion of the male medical implement.

The details of one or more embodiments are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

FIG. 5 illustrates the male distal tip of an IV set approaching the opening of a cleaning device.

FIG. 6 shows the male distal tip in contact with the plunger of the cleaning device.

FIG. 7 shows the male distal tip fully inserted into the housing of the cleaning device.

FIG. 8 is a cut-away view of an alternative implementation of a cleaning device.

FIG. 9 illustrates the male distal tip approaching a cleaning device.

Like reference symbols in the various drawings indicate like elements.

DETAILED DESCRIPTION

This document describes a cleaning device in the form of a cap to attach to a male distal end of an IV set to disinfect the male distal end, and to protect that male distal end from contamination. In accordance with some implementations, a cleaning device is provided for a male medical implement having a male protrusion. The cleaning device includes a cap that defines an inner cavity having a top and a bottom, the top of the inner cavity defining an opening. The cap further defines a channel that extends from the bottom of the inner cavity to a bottom of the cap, the channel having a diameter that is smaller than a diameter of the inner cavity.

The cleaning device further includes a plunger in the inner cavity. The plunger includes a domed top surface, a shoulder below the domed top surface, and a rod member extending below the shoulder to a piercing end. The rod member further includes a number of crush ribs extending laterally from the rod member, the piercing end of the plunger extending into the channel such that the domed top surface and shoulder are positioned proximate the opening in an initial position. The plunger is configured to move toward the bottom of the cap as the domed top surface is contacted by the male protrusion of the male medical implement, to push the rod member and piercing end further into the channel, and such that the crush ribs contact an inner surface of the channel to inhibit reverse movement of the plunger.

The cleaning device further includes a cleaning material around the rod member between the shoulder and the crush ribs, the cleaning material at least partially containing a cleaning agent. The cleaning material is compressed between the bottom of the inner cavity and the shoulder of the plunger to release the cleaning agent around the shoulder to contact the male protrusion of the male medical implement.

Figures 1, 2:
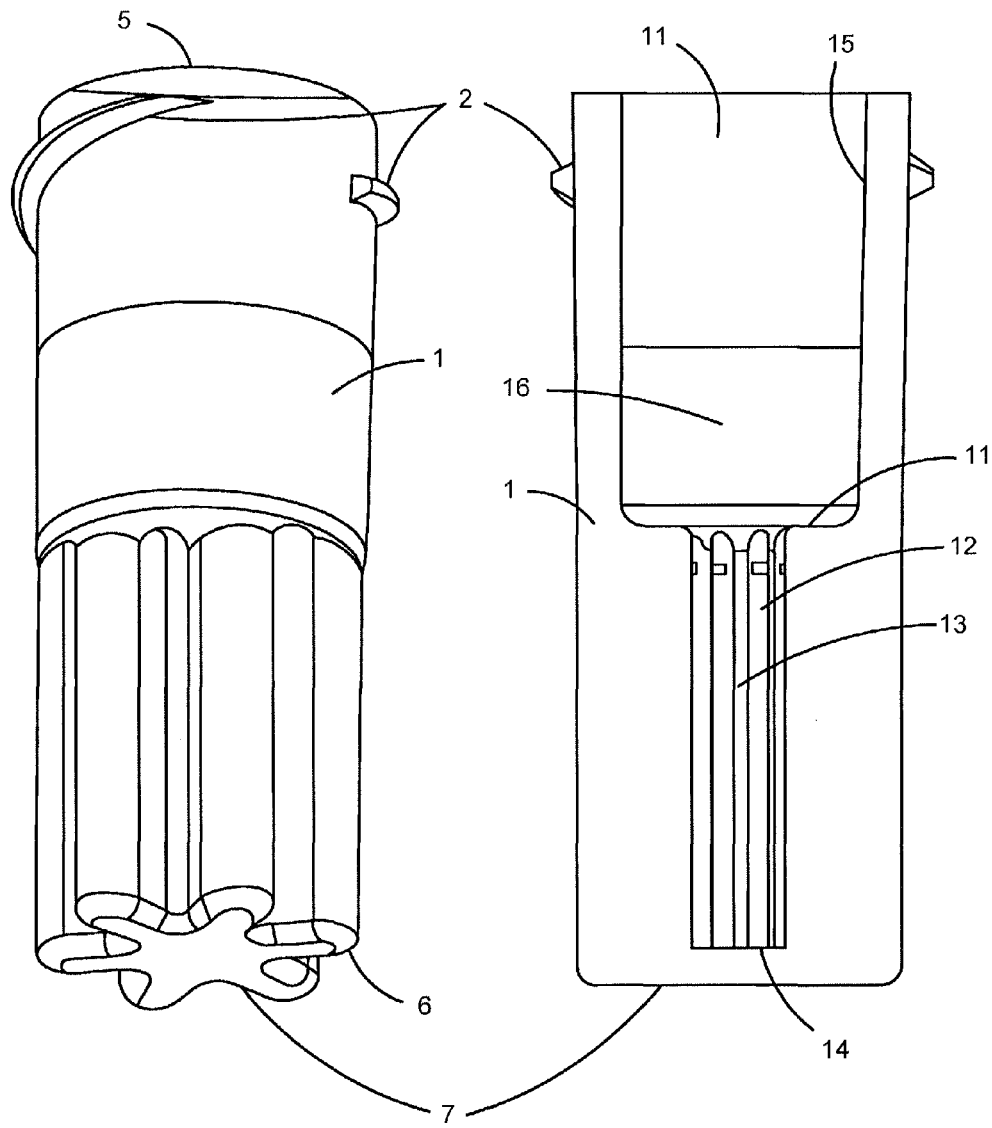
FIG. 1 is an isometric view of a cleaning device for a male luer end of an intravenous (IV) line.
FIG. 2 is a cut-away view of a housing of the device.

FIGS. 1-7 illustrate preferred exemplary implementations of a cleaning device for a male luer end of an intravenous (IV) line. In FIG. 1 an isometric view of a preferred implementation is shown. The housing (1) is a unitary body. The housing (1) may be constructed of any material compatible with the cleaning agent that is kept inside. Examples of materials would include silicone, rubber, high density polyethylene, polyurethane, etc. The housing (1) has an opening (5) large enough to allow the insertion of a medical device. Near the opening (5) are threads (2) that in the preferred embodiment are luer threads capable of coupling with other luer threads. As one will note, threads are just one means of attachment, a friction based attachment can also be used to attach to the inserted medical device, which in this case is the male distal end of an IV set or syringe. At the opposing end of opening (5) is closed end (7). Around the periphery of closed end (7) are ribs (6) which help facilitate the user's rotation of the housing. The ribs are which could result in the stripping of threads (2). Housing (1) with opening (5) and closed end (7) serve to create a cavity within the housing.

In FIG. 2 a cross-section of housing (1) is shown. Cavity (16) and plunger wall (13) are formed by opening (5) and closed-end (7). Cavity (16) is open at one end (11) and the other end (17) is closed except where plunger wall (13) begins. Plunger wall (13) is located in the center of the bottom of cavity (16). Plunger wall (13) is open into cavity (16) and has a closed-end (14). Plunger wall (13) is generally cylindrical except it has long channels (12) along its circumference traveling the length of plunger wall (13).

Figure 3:
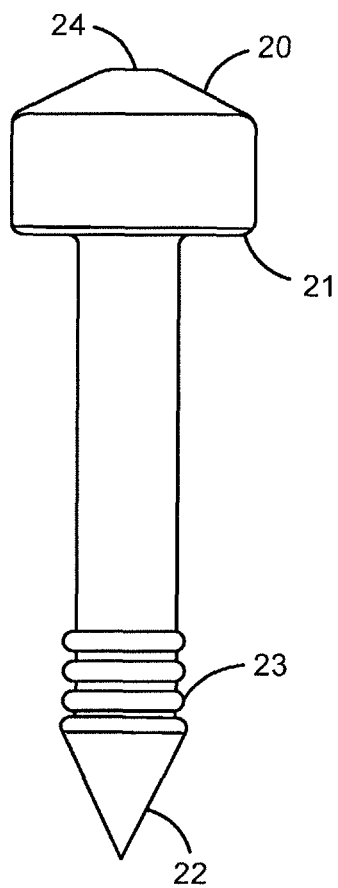
FIG. 3 is a view of a plunger of the device.

FIG. 3 is a view of the plunger (20). The plunger (20) can be constructed of the same material as the housing or any combination. The plunger (20) is comprised of a domed top-surface (24), a shoulder (21), crush ribs (23) and piercing end (22).

Figure 4:
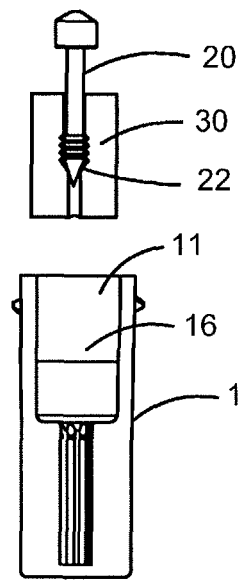
FIG. 4 is an assembly drawing showing the plunger in foam before insertion into the housing. Not shown are the seal and chemical agent.
Figure 10:
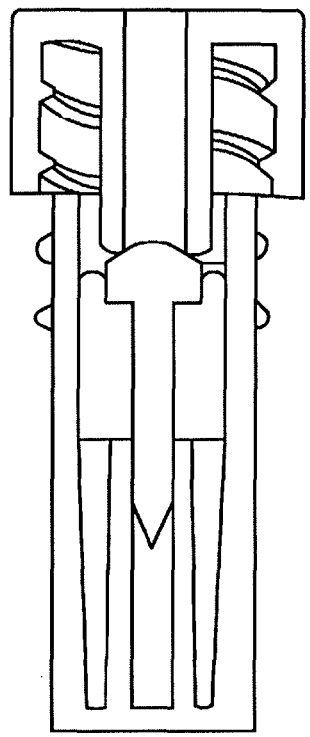
FIG. 10 shows the male distal tip in contact with the plunger of the cleaning device.

FIG. 4 illustrates an assembly of the cleaning device. This illustrates the plunger (20) piercing the compressible material (30). Piercing is achieved by pushing plunger piercing end (22) through the compressible material. This new assembly will then be pushed into housing (1) cavity (16) first through opening (11). The compressible material can be made to approximate cavity (16) dimensions. The piercing end (22) then seats itself into plunger wall (13) see FIG. 5. The foil seal and chemical agent are not shown.

The crush ribs (23) of piercing end (22) are slightly larger than the diameter of plunger wall (13) so that it acts as a brake on inadvertent movement. FIG. 5 shows a male luer (40) in relation to the assembled invention. FIG. 6 shows male luer (40) in contact with plunger (20). An area (24) of the plunger self-centers itself into the male luer's (40) open lumen (42). The dome (24) acts to seal or inhibit fluid flow into or out of open lumen (42). The male luer (40) has dimensions defined by an ISO standard. The wall (41) of the lumen (42) has a defined outer dimension and taper. The largest diameter is away from opening (42). The largest diameter of (41) is slightly smaller than the diameter of cavity (16). This dimensional difference creates a gap (11) between wall (41) and the wall of cavity (16). This gap is important because it allows the chemical agent to "wick" up the walls of (41) to disinfect these areas and the gap serves as a means to allow venting of extra pressures created within the housing as the male luer (40) is inserted. If this venting were not allowed then the chemical agent when compressed, would need to find escape, in this case it would be up through (42).

Figure 12:
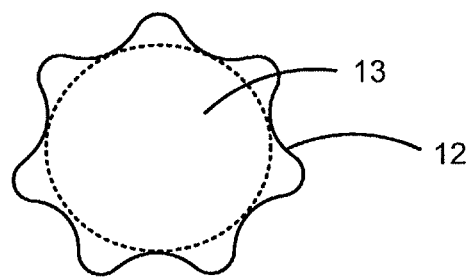
FIG. 12 is a top-down view of the cleaning device.

FIG. 7 shows the male luer (40) fully inserted into the housing. As the compressible material (30) is compressed it releases the chemical agent to clean, scrub and disinfect the male luer (40) and walls (41). As the male luer (40) continues its travel into the housing, the dome (24) remains seated to seal opening (42). The ribs (23) continue to act as a braking force to maintain dome (24) contact with opening (42). The plunger (20) can only be moved down into plunger wall (13) by the mechanical force of male luer (40) and its threads (43). Note the gap (11) still exists. Similarly, the plunger wall (13) must also be vented. As the plunger (30) moves down into wall (13) the trapped fluids and/or gases must vent or the unit may not function. Channels (12) serve that purpose. Attached is a cross-sectioned top view of the plunger wall FIG. 12. Accordingly, there is no need for biasing the plunger as with conventional devices.

Figure 11:
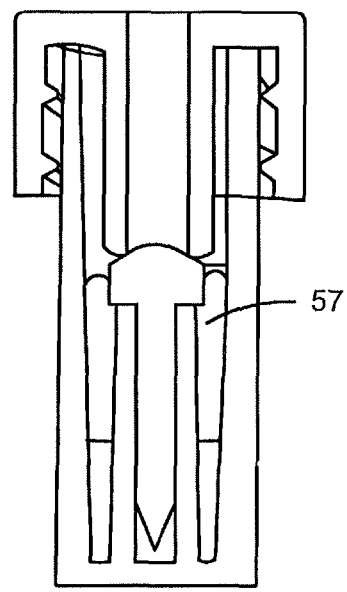
FIG. 11 shows the cleaning device fully engaged with a male luer end of an IV device.

FIGS. 8-11 illustrate various alternative implementations of a cleaning device. The main difference is in the plunger wall design. In FIG. 8, one can see the plunger wall is defined by two or more splines (50). As seen in FIG. 11, these splines hold the plunger assembly in place and splay outward to provide the braking force.

In the implementations described herein, chemical agents that could be used include, but not be limited to, isopropyl alcohol, chlorhexidone gluconate, chlorhexidone diacitate, povidone-iodine, ethanol, etc.

The lid (not shown), can be made from foil laminates or even non-paper materials that could be easily broken away to allow access. In preferred implementations, the lid is thermally or electrothermally bonded to or near the opening of the cap, and can be peeled away for cleaning the IV device. A lid in the configuration of a strip or planar piece of material could be configured to allow multiple devices to be placed on it, to allow each cap to be pulled away and used independently and separately. Alternatively, each cleaning device could be sealed and used on individual basis.

Although a few embodiments have been described in detail above, other modifications are possible. Other embodiments may be within the scope of the following claims.

The invention claimed is:

1. A cleaning device for a male medical implement having a male protrusion, the cleaning device comprising:
   a cap that defines an inner cavity having a top and a bottom, the top of the inner cavity defining an opening, the cap further defining a channel that extends from the bottom of the inner cavity to a bottom of the cap, the channel having a diameter that is smaller than a diameter of the inner cavity;
   a plunger in the inner cavity, the plunger includes a domed top surface, a shoulder below the domed top surface, and a rod member extending below the shoulder to a piercing end, the rod member further having a plurality of crush ribs extending laterally from the rod member, the piercing end of the plunger extending into the channel such that the domed top surface and shoulder are positioned proximate the opening, the plunger being configured to move toward the bottom of the cap as the domed top surface is contacted by the male protrusion of the male medical implement, to push the rod member and piercing end further into the channel, such that the crush ribs contact an inner surface of the channel to inhibit reverse movement of the plunger; and a compressible cleaning material around the rod member between the shoulder and the crush ribs, the compressible cleaning material at least partially containing a cleaning agent, the compressible cleaning material being compressed between the bottom of the inner cavity and the shoulder of the plunger as the domed top surface is being contacted by the male protrusion of the male medical implement, to release the cleaning agent around the shoulder to contact the male protrusion of the male medical implement.

2. A cleaning device for a male medical implement having a male protrusion, the cleaning device comprising:

a housing having an opening to an inner cavity the receive the male medical implement, and further having a channel extending from the inner cavity opposite the opening to a bottom of the housing, the channel having a diameter that is smaller than a diameter of both the opening and the inner cavity;

a compressible cleaning material in the inner cavity and at least partially containing a cleaning agent;

a plunger having a domed top surface, a shoulder below the domed top surface, and an elongated rod member extending below the shoulder that terminates at a piercing end, the rod member further having a plurality of crush ribs extending laterally from the rod member, the plunger being positioned within the housing such that, prior to receiving the male medical implement, the domed top surface and shoulder are positioned in the inner cavity proximate the opening, the plurality of crush ribs and piercing end are positioned in the channel proximate the inner cavity such that the crush ribs contact an inner surface of the channel to inhibit reverse movement of the plunger, and at least part of the elongated rod member between the plurality of crush ribs and the shoulder is surrounded by the compressible cleaning material;

the plunger being configured to move toward the bottom of the cap as the domed top surface of the plunger is contacted by the male protrusion of the male medical implement, to push the piercing end, the crush ribs and at least some of the elongated rod member further into the channel toward the bottom of the housing, and to compress the compressible cleaning material with the shoulder of the plunger in the inner cavity to release the cleaning agent around the shoulder to contact the male protrusion of the male medical implement.

3. The cleaning device in accordance with claim 2, wherein the inner cavity includes a widened side wall area to enable the cleaning agent to traverse the shoulder of the plunger after the male protrusion of the male medical implement has pushed the plunger further into the inner cavity and the channel.

4. The cleaning device in accordance with claim 2, further comprising threads that extend outwardly from an outer surface of the housing.

* * * * *